US00PP28095P3

(12) United States Plant Patent
Ranney

(10) Patent No.: US PP28,095 P3
(45) Date of Patent: Jun. 13, 2017

(54) ***VIBURNUM* PLANT NAMED 'NCVX1'**

(50) Latin Name: ***Viburnum* hybird**
Varietal Denomination: NCVX1

(71) Applicant: Thomas Green Ranney, Arden, NC (US)

(72) Inventor: Thomas Green Ranney, Arden, NC (US)

(73) Assignee: North Carolina State University, Raleigh, NC (US)

( * ) Notice: Subject to any disclaimer, the term of this patent is extended or adjusted under 35 U.S.C. 154(b) by 56 days.

(21) Appl. No.: 14/545,789

(22) Filed: Jun. 19, 2015

(65) Prior Publication Data

US 2016/0374240 P1 Dec. 22, 2016

(51) Int. Cl.
*A01H 5/02* (2006.01)

(52) U.S. Cl.
USPC ..... Plt./226

(58) Field of Classification Search
USPC ..... Plt./226
See application file for complete search history.

(56) References Cited

PUBLICATIONS

UPOV hit on *Viburnum* named 'NCVX1', CA PBR 14-8430, published Oct. 31, 2014.*

* cited by examiner

*Primary Examiner* — Anne Grunberg
(74) *Attorney, Agent, or Firm* — Cassandra Bright

(57) ABSTRACT

A new and distinct *Viburnum* cultivar plant named 'NCVX1' is disclosed, characterized by highly glossy, semi-evergreen foliage, which exhibits Fall color of red to purple. Plants are compact with a uniquely prostrate branching habit. Abundant cymes are produced with 150 to 400 florets. The new variety is a *Viburnum* normally produced as an outdoor garden or container plant.

4 Drawing Sheets

Figure 1:
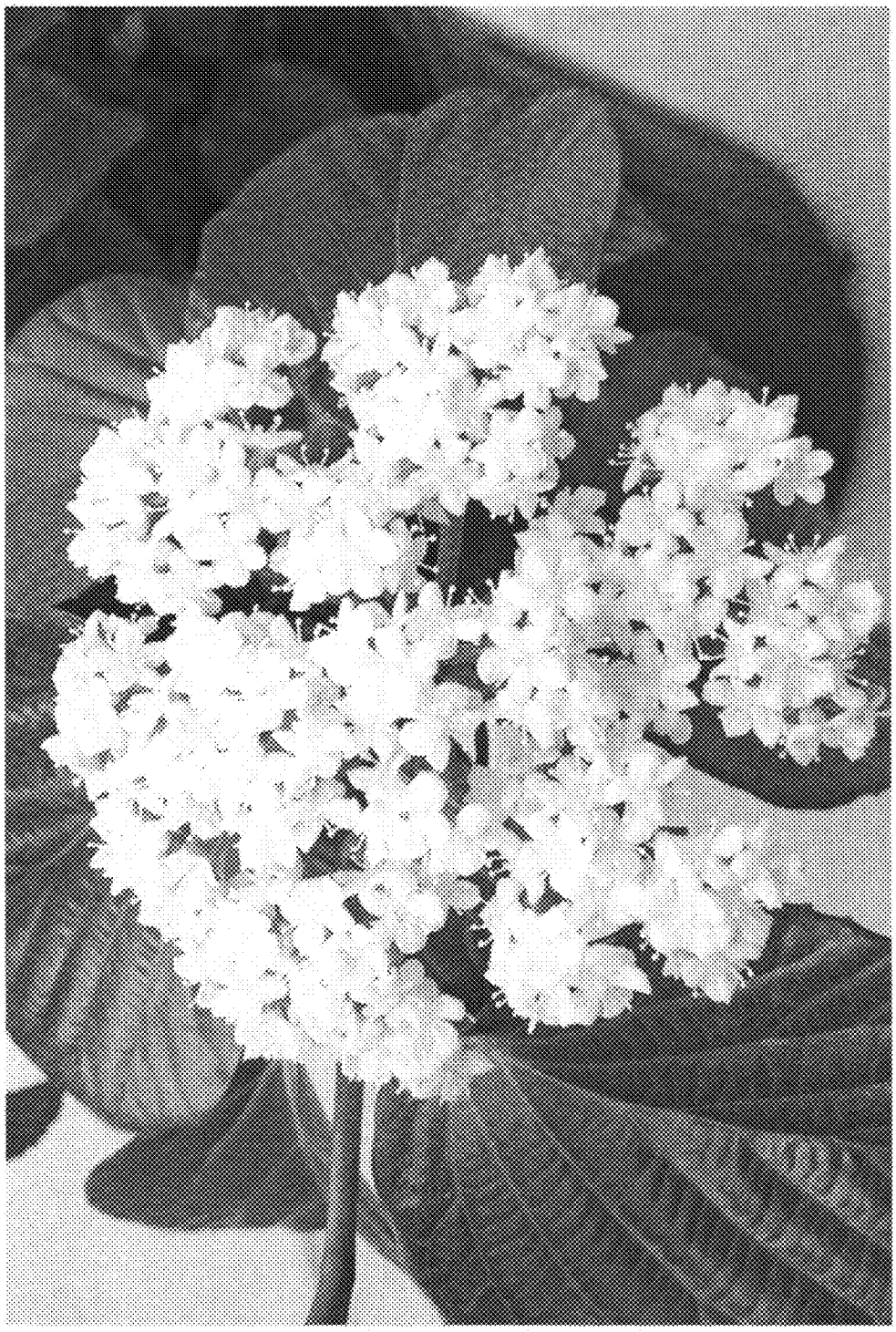

Classification: *Viburnum* hybrid.
Variety denomination: 'NCVX1'.

BACKGROUND OF THE INVENTION

The present invention comprises a new and distinct variety of *Viburnum*, hereinafter referred to by the cultivar name 'NCVX1'. This new *Viburnum* was developed through a breeding program at North Carolina State University, Mills River, N.C. 'NCVX1' was selected from a population of seedlings grown from an open-pollinated $F_1$ hybrid *Viburnum* (*lobophyllum*×*japonicum*) 'Huron' (unpatented) growing in an isolation block with *Viburnum* (*japonicum*×*dilatatum*) 'Chippewa' (unpatented).

The first asexual propagation of 'NCVX1' was carried out in July 2009 by rooting stem cuttings at the North Carolina State University, Mountain Horticultural Crops Research Station, Mills River, N.C. and has been asexually reproduced repeatedly by vegetative cuttings and in tissue culture over a 5 year period. 'NCVX1' roots readily from softwood cuttings treated with a basal dip of 4,000-5,000 ppm indole butyric acid (potassium salt) in water. 'NCVX1' has been found to retain its distinctive characteristics through successive asexual propagations.

SUMMARY OF THE INVENTION

The following are the most outstanding and distinguishing characteristics of this new cultivar when grown under standard horticultural practices at North Carolina State University, Mountain Horticultural Crops Research Station, Mills River, N.C.

1. Compact form with dense, prostrate, branching habit.
2. Semi-evergreen with highly glossy foliage.
3. Abundant cymes containing 150-400 small white florets.
4. Red to purple fall and winter foliage color.

COMPARISON WITH PARENTS

'NCVX1' is distinguished from its female parent *Viburnum* 'Huron' by its growth habit and foliage. 'NCVX1' has a compact, prostrate habit and extremely glossy, semi-evergreen leaves. *Viburnum* 'Huron' is a large upright shrub with dull, semi-evergreen leaves. 'NCVX1' is distinguished from *Viburnum* 'Chippewa' in that 'NCVX1' has a compact, mounding habit and *Viburnum* 'Chippewa' is a large, upright, rounded shrub.

COMPARISON WITH COMMERCIAL VARIETIES

'NCVX1' is similar in most horticultural characteristics to *Viburnum* 'Heneke' U.S. Plant Pat. No. 12,870. The new variety however differs in the following:

1. 'NCVX1' has a red flush to the mature foliage, this comparator has entirely green foliage.
2. 'NCVX1' has burgundy Fall foliage, not seen in this comparator.

'NCVX1' can also be compared to *Viburnum* 'Michael Dodge', unpatented. The new variety however differs in the following:

1. 'NCVX1' has dark green foliage with a red flush. 'Michael Dodge' has light green foliage.

2. 'NCVX1' has broader and rounder foliage than 'Michael Dodge'.
3. 'NCVX1' has burgundy Fall foliage. 'Michael Dodge' has orange Fall foliage.

DESCRIPTION OF THE PHOTOGRAPHS

This new *Viburnum* is illustrated by the accompanying photographs which show the plant's form, foliage and inflorescences. The colors shown are as true as can be reasonably obtained by conventional photographic procedures.

FIG. 1. Shows cymes with multiple florets in April 2014 in Mills River, N.C.

Figure 2:
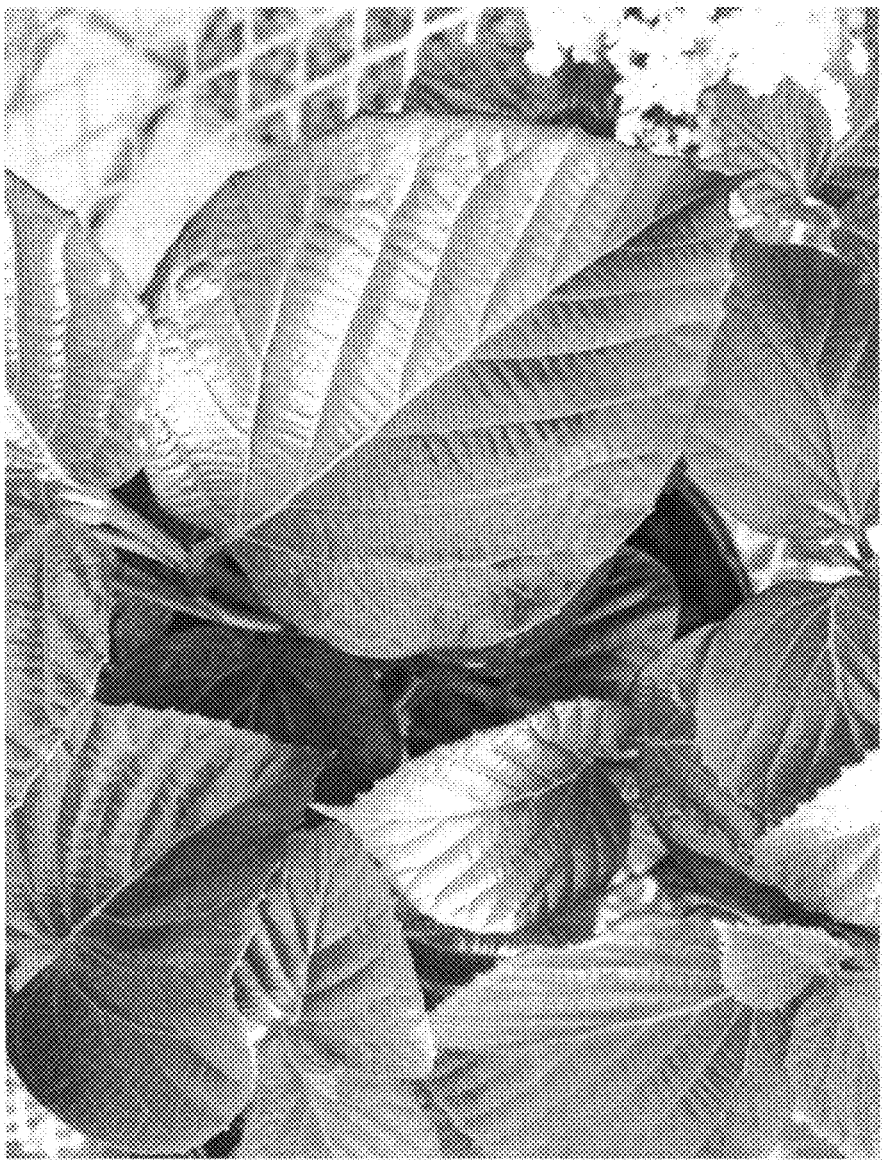

FIG. 2. Shows glossiness of foliage of a young container-grown plant in April 2014 in Mills River, N.C.

Figure 3:
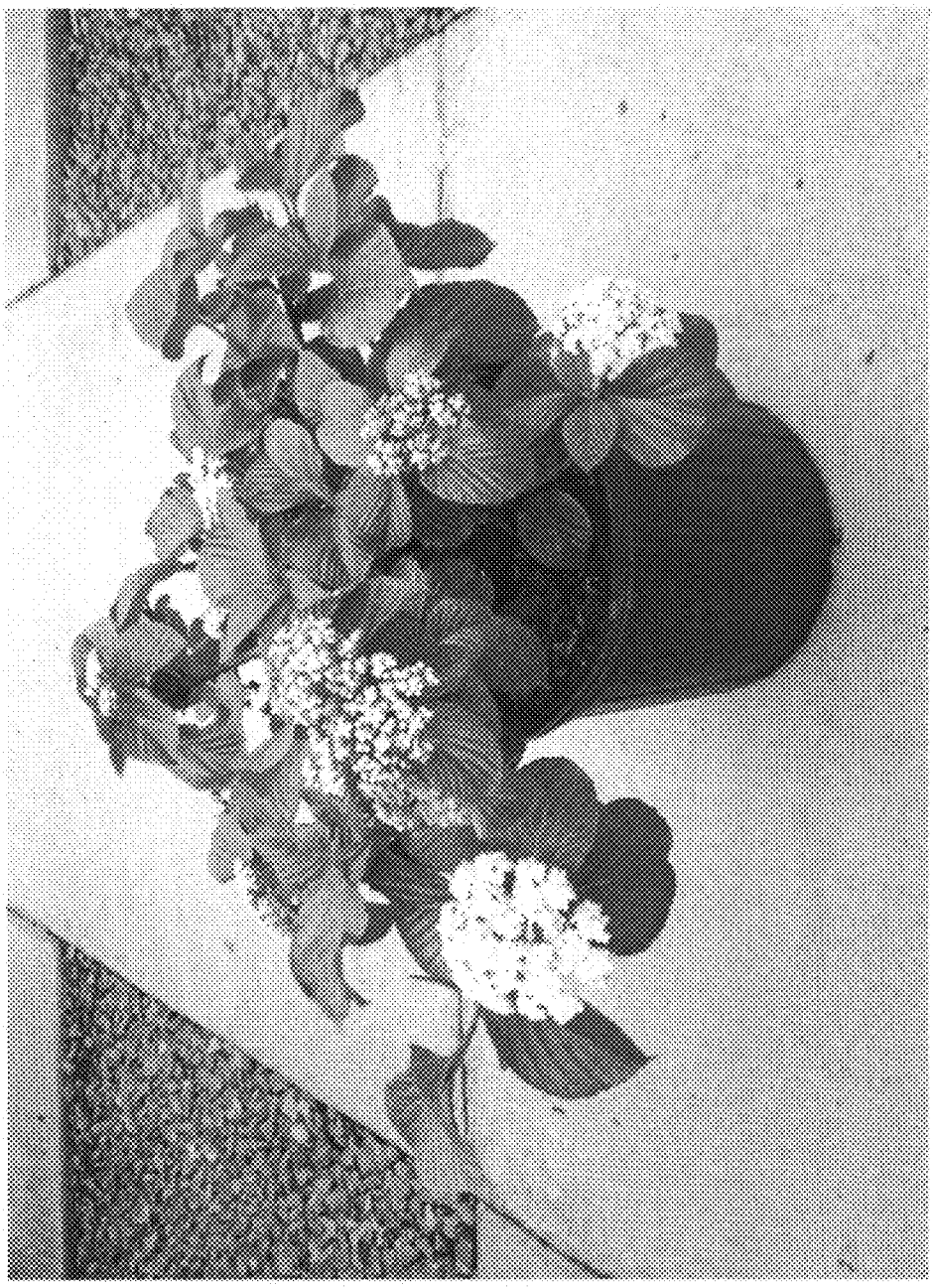

FIG. 3. Shows the overall habit of a container-grown plant in April 2014 in Mills River, N.C.

Figure 4:
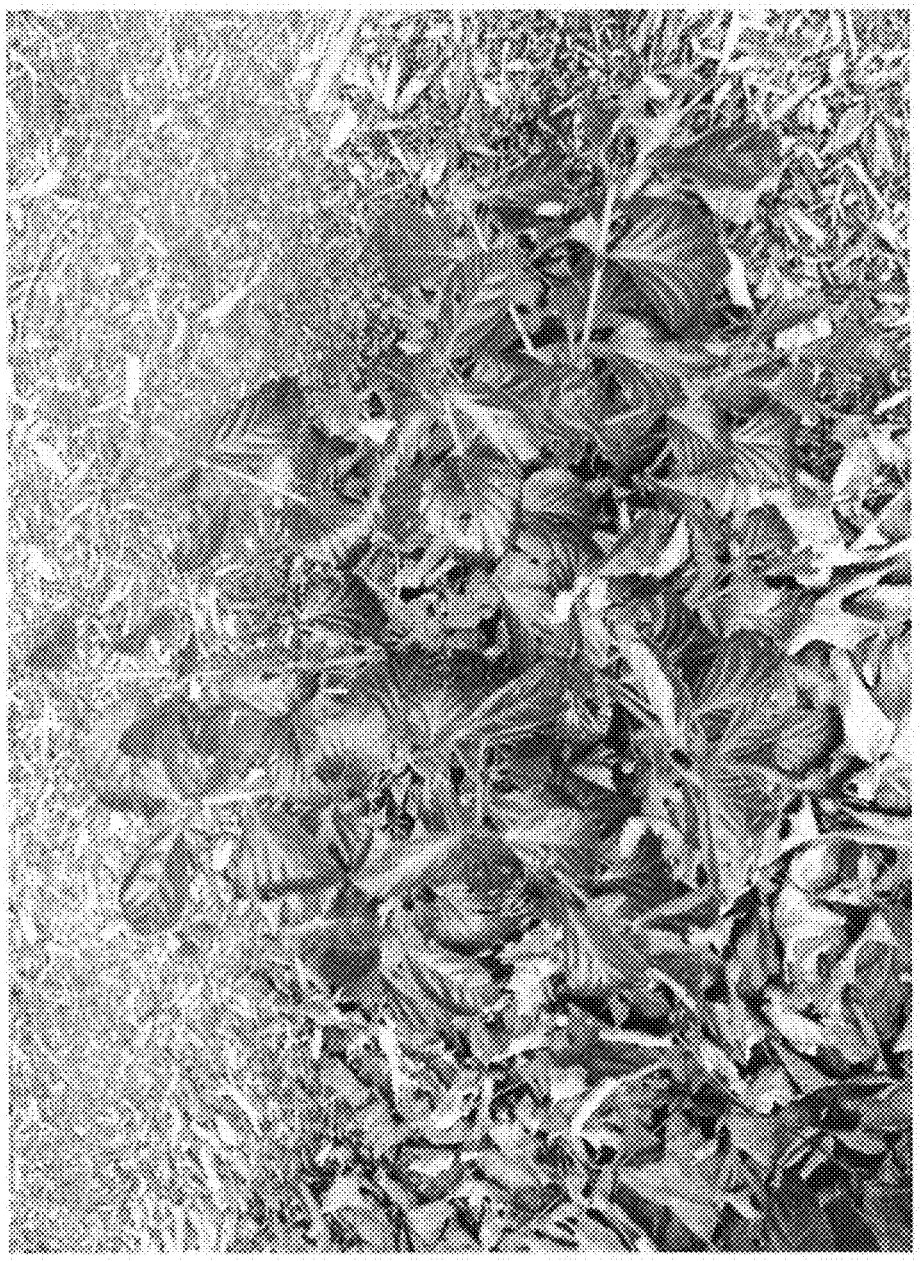

FIG. 4. Shows the fall and winter foliage color in November 2013 in Arden, N.C.

DESCRIPTION OF THE NEW CULTIVAR

The following detailed description sets forth the distinctive characteristics of 'NCVX1'. The detailed description was taken on 4-year-old plants growing in Mills River, N.C. in April 2014. Color references are to The R.H.S. Colour Chart of The Royal Horticultural Society of London (R.H.S.), 2001 Edition.

DETAILED BOTANICAL DESCRIPTION

Classification:

*Botanical name.*—*Viburnum* 'NCVX1'.

*Common name.*—*Viburnum.*

Parentage: Seedling from an open-pollinated, $F_1$ hybrid *Viburnum* (*lobophyllum*×*japonicum*) 'Huron' (unpatented) growing in an isolation block with *Viburnum* (*japonicum*×*dilatatum*) 'Chippewa' (unpatented).

Plant description:

*Growth habit.*—Prostrate to rounded with compact, dense branching habit.

*Height.*—50-55 cm at maturity.

*Width.*—70-80 cm at maturity.

Stem:

*Immature stem texture.*—Finely pubescent, lenticelled.

*Immature stem color.*—Yellow-Green (146C) flushed Greyed-Purple (183B).

*Mature stem texture.*—Glabrous, lenticelled.

*Mature stem color.*—Grey-Brown (N199A).

*Lateral branch length.*—Avg. 25 cm (typical range: 18 to 35 cm).

*Internode length.*—5 to 10.5 cm.

Foliage:

Leaves:

*Persistence.*—Semi-evergreen or tardily deciduous.

*Arrangement.*—Opposite, simple.

*Length.*—Avg. 11.3 cm (typical range: 8.0 to 13.0 cm).

*Width.*—Avg. 7.7 cm (typical range: 5.8 to 10.0 cm).

*Shape.*—Ovate to broad-ovate.

*Apex.*—Acute to acuminate.

*Base.*—Rounded.

*Venation pattern.*—Pinnate.

*Margin.*—Entire, undulate, toothed at apex.

*Emerging leaves.*—Color: Upper: Yellow-Green (144A) flushed with Red (46B). Lower: Yellow-Green (146C). Texture: Glossy, sparsely pubescent on both sides.

*Mature leaves during growing season.*—Color: Upper: Grayed-Green (N 189). Lower: Yellow-Green (147B). Venation: Grey-Purple (183C) to Yellow-Green (146D), both upper and lower sides. Texture: Upper side glossy and slightly pubescent; glabrous below.

*Fall foliage color.*—Upper: Ranging between and including Greyed-Red (178A) to Greyed-Purple (183A). Lower: Yellow-Green (147C).

*Petiole.*—Length: Avg. 1.5 cm (typical range: 1.2 to 2.0 cm). Width: Avg. 0.18 cm (typical range: 0.15 to 0.22 cm). Texture: Slightly pubescent. Color: Yellow-Green (146C), upper and lower.

Inflorescence:

*Description.*—Rounded, umbel-like cyme.

*Number of flowers per inflorescence.*—150-400.

*Flowering season.*—Early May.

*Flower longevity.*—2-3 weeks.

*Fragrance.*—None.

*Inflorescence height.*—Avg. 4.0 cm (typical range: 3.0 to 5.0 cm).

*Inflorescence diameter.*—Avg. 9.0 cm (typical range: 7.5-10.5 cm).

*Flower diameter.*—Avg. 0.58 cm (typical range: 0.5 to 0.8 cm).

*Flower depth.*—Avg. 0.38 cm (typical range: 0.25 to 0.4 cm).

*Flower bud.*—Length: Less than 0.2 cm. Diameter: Less than 0.2 cm. Shape: Round. Color: Ranging from Yellow-Green (150C) to White (155A).

*Petals.*—Number: 5. Length: Avg. 0.3 cm (typical range: 0.26 to 0.32 cm). Width: Avg. 0.26 cm (typical range: 0.23 to 0.29 cm). Shape: Obovate. Apex: Obtuse. Base: Fused. Texture: Glabrous. Color: White (155C).

*Sepals.*—Number: 5. Length: Less than 0.1 cm. Width: Less than 0.1 cm. Shape: Deltoid. Apex: Acute. Base: Fused. Margin: Entire. Texture: Glabrous. Color: White (155C).

*Peduncle.*—Length: Avg. 1.56 cm (typical range: 1.2 to 2.5 cm). Width: Avg. 0.12 cm (typical range: 0.08 to 0.15 cm). Color: Yellow-Green (146C to 146D). Texture: Glabrous.

*Pedicels.*—Length: Avg. 0.32 cm (typical range: 0.15 to 0.5 cm). Diameter: Less than 0.1 cm. Texture: Glabrous. Color: Yellow-Green (146C to 146D).

Reproductive organs:

*Gynoecium.*—Pistil number: About 3. Pistil length: About 0.05 cm. Stigma shape: 3-lobed. Stigma color: White (155C). Style length: Less than 0.05 cm. Style color: White (155C).

*Androecium.*—Stamen number: 5. Anther shape: Round. Anther width: Less than 0.05 cm. Anther color: Orange-White (159B). Amount of pollen: Scarce. Pollen color: White (155C).

OTHER CHARACTERISTICS

Fruit/seed set: None observed.

Disease and insect resistance: No significant disease or insect pests have been observed.

Cold hardiness: At least USDA zone 6b; testing not completed in colder zones.

What is claimed is:

1. A new and distinct *Viburnum* plant named 'NCVX1' as illustrated and described herein.

* * * * *